United States Patent [19]

Marquez et al.

[11] Patent Number: 5,495,010
[45] Date of Patent: Feb. 27, 1996

[54] ACID STABLE PURINE DIDEOXYNUCLEOSIDES

[75] Inventors: Victor E. Marquez, Gaithersburg; John S. Driscoll, Rockville; Christopher K-H. Tseng, Burtonsville; James A. Kelley, Silver Spring; David G. Johns, Bethesda; Hiroaki Mitsuya, Rockville, all of Md.

[73] Assignee: The United States of America as represented by the Department of Health and Human Services, Washington, D.C.

[21] Appl. No.: 762,082

[22] Filed: Sep. 19, 1991

Related U.S. Application Data

[63] Continuation of Ser. No. 288,652, Dec. 12, 1988, abandoned, which is a continuation-in-part of Ser. No. 39,402, Apr. 17, 1987, abandoned.

[51] Int. Cl.$^6$ .................................................... C07H 19/16
[52] U.S. Cl. .................. 536/27.14; 536/27.6; 536/27.8; 536/27.81
[58] Field of Search ........................... 536/26, 26.7, 27.1, 536/27.13, 27.14, 27.6, 27.8, 27.81; 514/45, 46, 885

[56] References Cited

U.S. PATENT DOCUMENTS

| | | | |
|---|---|---|---|
| 2,928,773 | 3/1960 | Klein | 435/88 |
| 4,145,531 | 3/1979 | Eckstein et al. | 536/27.11 |
| 4,625,020 | 11/1986 | Brundidge et al. | 536/18.2 |
| 4,666,892 | 5/1987 | Fox et al. | 514/49 |
| 4,751,221 | 6/1988 | Watanabe et al. | 514/46 |
| 4,788,181 | 11/1988 | Driscoll et al. | 514/49 |
| 4,880,782 | 11/1989 | Eckstein et al. | 514/45 |
| 4,882,316 | 11/1989 | Lambert et al. | 514/49 |
| 4,886,785 | 12/1989 | Lambert et al. | 514/50 |
| 4,918,056 | 4/1990 | Bobek et al. | 514/25 |
| 4,963,662 | 10/1990 | Matthes et al. | 514/45 |

OTHER PUBLICATIONS

Herdewijn et al., J. of Med. Chem., vol. 30, pp. 2131–2137 (1987).
Pauwels et al., Biochemical Pharmacology, vol. 37, No. 7, pp. 1317–1325, (1988).
Sandstrom et al., Drugs, vol. 34, pp. 372–390, (1987).
Mitsuya et al., Retroviruses In Human Lymphoma/Leukemia, pp. 277–288, (1985).
Hamilton, The Wall Street Journal, 11 Aug. 1994, Section B, p. 6.
Barnett et al., Science, vol. 266, 28 Oct. 1994, pp. 642–646.
Harada et al., "Synthesis and Anticytomegalovirus And Antiherpes Simplex Virus Activity of 5'-Modified Analogues of 2'-Fluoroarabinosyl pyrimidine Nucleosides", (1987) J. Med. Chem. vol. 30:226–229.
Watanabe et al., J. Med. Chem., vol. 27, pp. 91–94 (1984).
Cheng et al., J. Biol. Chem., vol. 262, No. 5, pp. 2187–2189 (1987).
Lin et al., Biochem. Pharmacol., vol. 36, No. 3, pp. 311–316 (1987).
Mikhailov et al., Bioorg. Khim., vol. 12, No. 5, pp. 626–632 (1986).

*Primary Examiner*—Douglas W. Robinson
*Assistant Examiner*—James O. Wilson
*Attorney, Agent, or Firm*—William S. Feiler; Mary J. Morry; Robert Benson

[57] ABSTRACT

Purine nucleosides active against human immunodeficiency virus which are substituted at the 2'-position by a strong electronegative group such as fluorine are stable in an acid environment and thus can be used for oral administration.

4 Claims, 3 Drawing Sheets

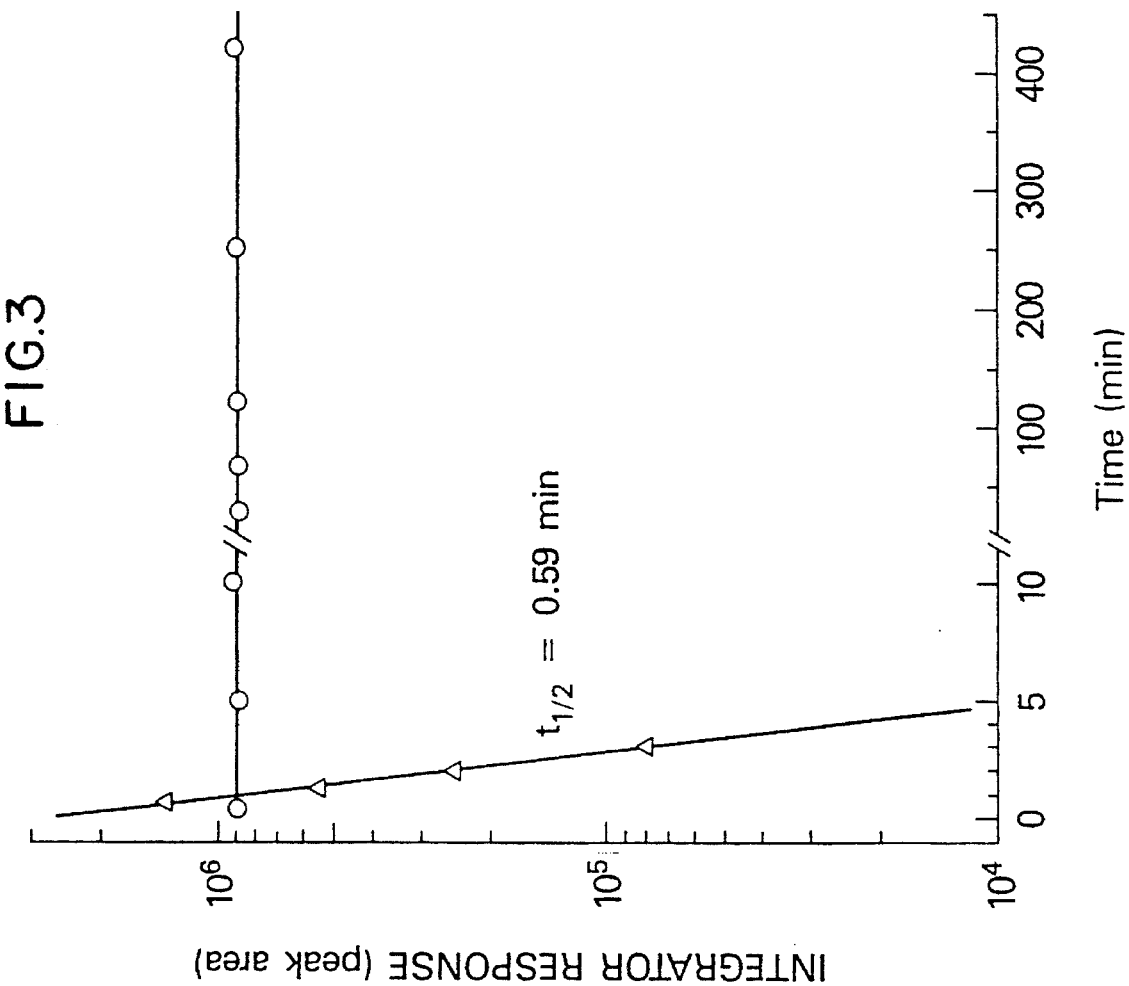

ACID STABLE PURINE DIDEOXYNUCLEOSIDES

This is a continuation of application Ser. No. 07/288,652, filed on Dec. 12, 1988, now abandoned, which is a CIP of 07/039,402, which was filed on Apr. 17, 1987, which is abandoned.

FIELD OF THE INVENTION

The present invention relates to dideoxynucleosides which are suitable in acid environments, such as found in the human stomach.

BACKGROUND OF THE INVENTION

Acquired immune deficiency syndrome, or AIDS, is a fatal disease which has reached epidemic proportions among certain high risk groups. Several features of AIDS make therapy extremely difficult. The main target of the AIDS virus, now known as HIV, or human immunodeficiency virus, is the T4 lymphocyte, a white blood cell that marshals the immunize defenses. This depletion of T4 cells in AIDS causes a severe depression of the immune response, so that a compound which is to be effective against AIDS must modify virus effect without much help from host immunity. Furthermore, the virus also affects cells in the central nervous system, where it is protected by the blood-brain barrier from compounds that might otherwise be effective against the virus. In infecting its host, the HIV binds to specific cell-surface receptor molecules. The virus penetrates the cell cytoplasm and sheds its protein coat, thereby baring its genetic material, a single strand of RNA. A viral enzyme, reverse transcriptase, accompanies the RNA. The virus which is, a retrovirus, reverse transcribes the RNA into DNA. Ultimately, some DNA copies of the HIV genome become integrated into the chromosomes of the host cell.

This integrated viral genome, known as a provirus,. may remain latent until the host cell is stimulated, such as by another infection. The provital DNA is then transcribed into DNA, which directs the synthesis of viral proteins. The provirus also gives rise to other RNA copies that will serve as the genetic material of viral progeny. The proteins and the genomic RNA congregate at the cell membrane and assemble to form new HIV particles, which then break off from the cell. Two HIV genes, tat and trs/art, appear to control this burst of replication, which destroys the cell. These genes code for small proteins that boost the transcription of proviral DNA and the synthesis of vital proteins.

Several compounds have been known to reduce the activity of reverse transcriptase in vitro. The reverse transcription is the step that is essential to viral replication and irrelevant to host cells. It has been found that HIV replication is considerably slower in the presence of compounds such as suramin, antimoniotungstate, phosphonoformate, and a class of nucleoside analogues known as dideoxynucleosides.

Nucleoside analogues are a class of synthetic compounds that resemble the naturally occurring nucleosides, which are chemical precursors of DNA and RNA. A nucleoside comprises a single-or double-ring base linked to a five-carbon sugar molecule. An analogue differs from the naturally-occurring nucleoside in large or small features of the base or the sugar. An enzyme that normally acts on a nucleoside in the course of viral replication can also bind to the nucleoside analogue. Because the nucleoside and time analogue differ, however, binding to the analogue can incapacitate the enzyme, thereby disrupting a molecular process crucial to viral replication.

Of the synthetic nucleoside analogues, dideoxyadenosine (ddA), dideoxyinosine (ddI) and dideoxycytidine (ddC), have been found to have potent in vitro activity against the human immunodeficiency virus (HIV) which causes AIDS. Additionally, dideoxycytosine has been found effective in vivo in treating patients with AIDS, and dideoxyinosine and dideoxyadenosine are currently being tested in vive in patients with AIDS. Because the activated form of dideoxynucleosides (5'-triphosphate) appears to inhibit the replication of the virus at the stage of reverse transcription of de novo infection of the virus, it is most likely that a drug of this type must be taken continuously if the therapeutic effect is to be maintained. Since daily treatment for a long period might ensue, oral drug administration is envisioned as the most practical route for a patient population numbering in the thousands.

Drugs administered orally are exposed to a pH range of 1 to 2 in the human stomach environment for approximately one hour. This could result in drug stability problems with ddA, since this compound undergoes acid-catalyzed hydrolysis of the glycosidic bond at a rate 40,000 times faster than adenosine. It was found that ddA has a $t_{1/2}$ of 35 seconds at pH 1.0 at 37° C. (FIG. 3). Cleavage of this compound not only reduces its efficacy, but potential problems of toxicity may occur due to formation of excessive quantities of one of the cleavage products.

SUMMARY OF THE INVENTION

It is an object of the present invention to provide synthetic nucleosides which are useful in treating AIDS.

It is another object of the present invention to provide synthetic nucleosides which are stable in an acid environment.

It is a further object of the present invention to provide synthetic nucleosides which inhibit the infectivity of the human immunodeficiency virus.

It is yet a further object of the present invention to provide synthetic nucleosides which can be administered orally to treat acquired immune deficiency syndrome.

It is yet another object to overcome deficiencies in the prior art, such as indicated above; and still a further object to advance AIDS therapy.

The compounds of the present invention have potent activity against the HIV virus, the virus which causes AIDS. These compounds are also stable to the acidic conditions which exist in the human stomach, pH 1–2.

Purine nucleosides active against human immunodeficiency virus which are substituted at the 2'-position by a strong electronegative group such as fluorine are stable in an aid environment such as the human stomach, and thus are useful for oral administration.

The compounds of the present invention have the following formulae:

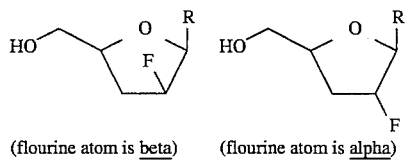

(flourine atom is beta)    (flourine atom is alpha)

wherein R is selected from the group consisting of

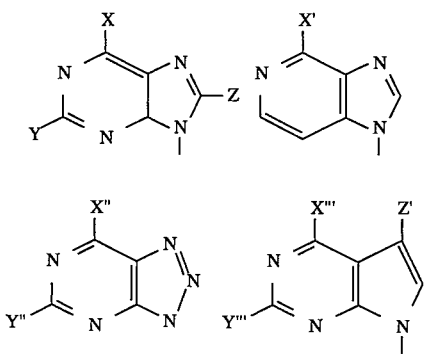

wherein X, Y and Z are independently selected from the group consisting of H, aryl, alkyl, acyl, SH, $NH_2$, OH, halogen, NH-alkyl, N(dialkyl), NH-aryl, NH-acyl, $N[Si(CH_3)_3]_2$, O-alkyl, O-acyl, O-aryl and fluoroalkyl.

halogen is selected from the group consisting of F, Cl, Br, and I;

alkyl is selected from the group consisting of $C_1$–$C_8$ alkyl and hydroxyalkyl; aryl is selected form the group consisting of phenyl and phenyl substituted with alkyl and phenyl substituted with OH;

acyl is selected from the group consisting of CO-alkyl and CO-aryl;

X' is selected from the group consisting of $NH_2$, and OH;

X" and Y" are independently selected from the group consisting of H, OH, $NH_2$, and halogen;

X''' and Y''' are independently selected from the group consisting of H, OH, $NH_2$, and halogen;

Z' is selected from the group consisting of H, CN, $CONH_2$, and alkyl.

DESCRIPTION OF THE DRAWINGS

FIG. 3 shows the rate of decomposition for 2',3'dideoxyadenosine (Δ) and 2'-beta-fluoro-2',3'-dideoxyadenosine (O) at pH 1 and 37° C.

DETAILED DESCRIPTION OF THE INVENTION

Figure 1:
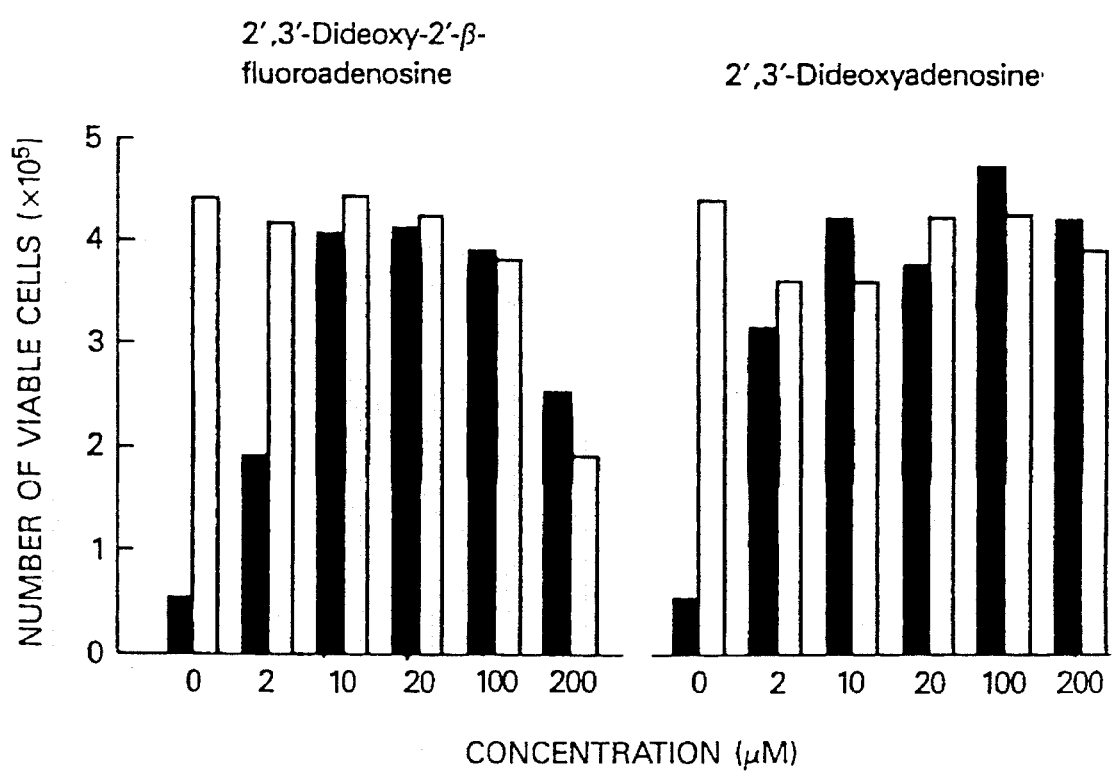
FIG. 1 shows the activity and potency of ddA and the 2'-beta-fluoro derivative (III) of ddA against HIV.
Figure 2:
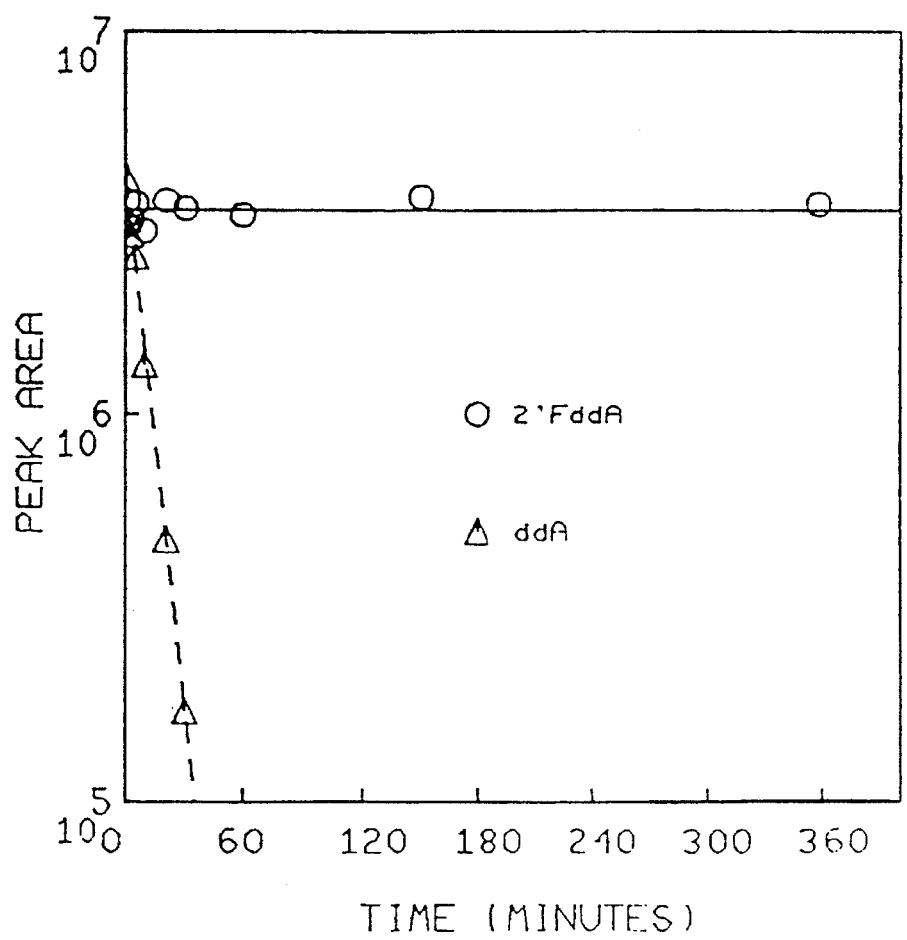
FIG. 2 shows the stability of: 2,3-dideoxyadenosine (I) and 2',3'-dideoxy-2'-alpha-fluoroadenosine (II) in an environment of pH 2 at 37° C.

In order to study acid-catalyzed decomposition of the subject compounds, a pH 1 buffer was prepared by dissolving 0.746 g KCl and 26.8 g 1.0 N HCl in sufficient distilled water to give 200 ml total volume. Ten ml of buffer, prewarmed to 37° C., was added to each of 102 micrograms of ddA (Compound I), and 93 micrograms of compounds II and III, 2',3'-dideoxy-2'-alpha-fluorodeminine and 2'-beta-fluoro-2',3'-dideoxyadenosine. The samples were shaken and maintained at 37° C. Aliquots were taken at timed intervals and neutralized immediately with 0.1 NaOH and chilled on ice. The amount of ddA and each of the other fluorinated analogs were determined by HPLC analysis using a 4.6×250 mm 5 microgram Ultrasphere ODS column protected by a guard column packed with 37–50 micron Vydac 201SC. Elution was with 12% acetonitrile in 0.01M pH 6.8 phosphate bugger at 1.0 ml/minute. The integrator peak areas were plotted as a function of time, and the data was fitted to a first order decomposition curve by a computer program (MLAB).

To test the cytopathic effect of the compounds of the present invention, a HIV cytopathic assay was performed using ATH8 cells as described by Mitsuya et al., Proc. Nat. Acad. Sci. USA, 83, 1911 (1986). In brief, 2×10⁵ ATH8 cells were preexposed to polybrene, exposed to HTLV-IIIB virus (2000 virus particles/cell) for 45 minutes after treatment with polybrene, resuspended in 1 ml of culture medium containing Interleukin 2 in the presence or absence of various concentrations of compounds, and incubated in culture tubes at 37° C. in 5% $CO_2$/95% air humidified atmosphere. Control cells were treated similarly but were not exposed to the virus. At various times of days 5 to 7 of culture, the total viable cells were counted in a hemocytometer by the trypan blue dye exclusion method. In the HIV cytopathic effect assay using ATH8 cells, 0.5 to 5 virus particles per cell represent the minimum cytopathic dose of the virus.

The 2'-alpha- and 2'-beta-fluoroisomers of 2',3'-dideoxyadenosine, compounds II and III, were synthesized as described below.

The alpha-isomer was obtained in four steps from 3'-deoxy-ara-A. The 5'-hydroxyl group was protected with dimethoxytrityl chloride, and the 2'-hydroxyl group was activated by formation of the corresponding triflate derivative. The configuration of the 2'-position was inverted by aim SN2 displacement using tetra-n-butylammonium fluoride. The dimethoxytrityl protective group was removed with dichloroacetic acid. The nucleophilic displacement of triflate by fluoride ion gave compound II as a lyophilized white powder, Rf 0.25 ($SiO_2$, $CHCl_3$ :$CH_3OH$ ::9:1); m/z calc. $C_{10}H_{13}N_5O_2F$ (MH+)254.1052, found 254.1059±0.0017. This was accompanied by a minor, olefin-forming reaction caused by elimination rather than displacement of the triflate group. A similar type of elimination reaction became exclusive when the same synthetic approach was applied to the preparation of the beta-isomer from 3'-deoxyadenosine (corcycepin).

The failure of the triflate displacement reaction required the development of an alternative approach for formation of the beta-isomer. This required the synthesis of the previously reported compound 6-amino-9-(beta-D-2'-deoxy-2'-fluoro-arabino-furanosyl)- 9-H-purine (2'-F-ara-A, compound VI), as a starting material. This intermediate, originally synthesized by Fox et al., J. Org. Chem., 34, 2632 (1969) was prepared using the improved general procedure of Montgomery et al., J. Med. Chem., 29, 2389 (1986). This improved procedure involved condensing 6-chloropurine with 3-0-acetyl-5-0-benzoyl-1-2-deoxy-2-fluoro-Darabino-furanosyl bromide. The required functionalized halogenosugar was prepared in essentially the same manner as reported by Fox et al., Carbohyd. Res., 42, 233 (1975). As expected, four isomers were obtained from the condensation reactions. After separation and characterization of the correct 6chloro isomer, the required starting material, 2'-F-ara-A, was obtained by ammonolysis with concentrated methanolic ammonia which simultaneously removed the protective groups. All of the chemical, optical, and spectral properties of the compound matched those reported for 2'-F-ara-A. Selective protection of the 5'hydroxyl function of this compound by reaction with t-butyldimethyl silyl chloride gave a product that permitted the two-step reduction of the 3'-hydroxyl group. Treatment with phenyl chlorothiocarbonate followed by reaction of the intermediate 3'-0-phenoxythiocarbonyl derivative with tri-n-butyl tin hydride, produced the desired 2',3'-dideoxynucleoside with the 2'-fluorine in the beta, or "up", configuration. This required only the removal of the 5'-blocking group with tetra n-butyl ammonium fluoride to give compound III as a white lyophilized product, Rf 0.18 (SiO$_2$, CHCl$_3$ :CH$_3$OH: :9:1); m/z calc. C$_{10}$H$_{13}$N$_5$O$_2$F (MH+) 254.1052, found 254.1031-0.0018.

It was found that 2',3'-alpha-fluorodideoxyadenosine, compound II, was stable to acid-catalyzed decomposition at pH 2; the addition of a fluorine atom in this "down" configuration gave the compound a protective effect against HIV of 25% that seen with ddA.

2',3'-dideoxy-2'-beta-fluoroinosine, compound IV, was prepared enzymatically from compound III, 2',3'-dideoxy-2'-betafluoroadenosine by treatment with adenosine deaminase (adenosine aminohydrolase, EC 3.5.4.4) One milligram of 2',3'-dideoxy-2'-beta-fluoroadenosine was dissolved in one ml water at room temperature, and 0.25 microliter of commercial adenosine deaminase enzyme solution, one unit, was added. The reaction, which was monitored by HPLC (260 nm, UV detection), was complete in one hour. Compound IV was also prepared from compound III by reaction with sodium nitrite in acetic acid.

Compound IV, 2',3'-dideoxy-2'-beta-fluoroinosine, has a HPLC retention time of 6.64 minutes using a 4.6×250 mm 5 microliter Beckman/Altex Ultrasphere ODS analytical column preceded by a Waters guard column (Vydak). The mobile phase used was 8.5% acetonitrile/0.01M phosphate buffer, at pH 6.8. Compound IV was obtained by ultrafiltration to remove the protein, followed by lyophilization.

It has been found that adenosine deaminase in the body causes the metabolism of 2',3'-dideoxy-2'-beta-fluoroadenosine to compound IV, 2',3'-dideoxy-2'-beta-fluoroinosine. Compound IV is also useful in inhibiting the infectivity of the HIV virus.

A change in the fluorine stereochemistry at the 2' position, however, produced dramatically better results. Compound III, 2'-beta-fluorodideoxyadenosine was approximately as active and potent as ddA in protecting ATH8 cells against the cytopathic effect of HIV, as shown in FIG. 1, under conditions of substantial viral excess. Furthermore, the antiviral effect of compound III was as durable as that of the parent compound, compound I. In addition, compound III was completely unchanged after a 24 hour exposure to acidic conditions at pH 1, as shown in FIG. 3. Based on the mechanism proposed for the acid decomposition of this compound, the increased stability of this compound as well as that of the alpha-isomer may be a consequence of the inductive destabilization by fluorine of the intermediate oxonium ion which would result from hydrolysis of the glycosidic bond. While fluorine is an ideal group to introduce because of its strong electronegative effect and size similarity to hydrogen, other electronegative groups in the 2'-position such as cyano, azido, nitro etc., should have acid stabilizing properties also.

Because the compounds of the present invention are stable in an acid environment such as is found in the human stomach, they call readily be formulated without the need for pH buffers into dosages suitable for oral administration, using pharmaceutically acceptable carriers, which carriers are well known in the art. Such carriers may enable the compounds to be formulated as tablets, pills, capsules, liquids, gels, and the like, for oral ingestion by a patient to be treated for AIDS.

The precise dosage amounts to be administered will be determined by routine experimentation. In general, however, the dosage amounts wall be comparable or less than those already known from the experimental use of dideoxy adenosine.

Pharmaceutical compositions within the scope of the present invention include compositions wherein the active ingredient is contained in an effective amount to achieve its intended purpose. Determination of the effective amounts is well within the skill of the art.

In addition to the purine nucleosides of the present invention, these pharmaceutical compositions may contain suitable pharmaceutically acceptable carriers comprising excipients and auxiliaries which facilitate processing of the active compounds into preparations which can be used pharmaceutically. Preferably, the preparations are formulated for oral administration, and are in the form of tablets, dragees, and capsules. Alternatively, the preparations may be administered rectally, such as in the form of suppositories. Alternatively, solutions may be prepared for oral or parenterally. The compositions of the present invention contain from about 0.1 to 99 percent, and preferably from about 25 to 85 percent by weight of active ingredient, together with the excipient.

The pharmaceutical compositions of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding a resulting mixture, and processing the mixture of granules, after adding suitable auxiliaries, if desired, to obtain tablets or dragee cores.

Suitable excipients are, in particular, fillers such as sugars, such as lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone. Of desired, disintegrating agents may be added, such as the cross-linked polyvinyl pyrrolidone, agar, or alginic acid or a salt thereof such as sodium alginate. Auxiliaries which can be used include flow-regulating agents and lubricants, such as silica, talc, stearic acid or salts thereof such as magnesium or calcium stearate, and/or polyethylene glycol. Dragee cores are provided with suitable coatings. For this purpose, concentrated sugar solutions may be used, which may optionally contain gum arabic, talc, polyvinyl pyrrolidone, polyethylene glycol, and/or titanium dioxide, lacquer solutions, and suitable organic solvents or solvent mixtures. Dyestuffs or pigments may be added to the tablets or dragee coatings for identification or in order to characterize different combinations of active compound doses.

Other pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols or higher alkanols. In addition, it is also possible to use gelatin rectal capsules which consist of a combination of the active compounds with a base. Possible base materials include, for example, liquid triglycerides, polyethylene glycols, or paraffin hydrocarbons.

Although the compounds of the present invention are designed to be administered orally because of their stability in low pH environments such as in gastric juices, pharmaceutical preparations may also be prepared for parenteral administration. Suitable formulation for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, and/or dextran. Optionally, the suspension may also contain stabilizers.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. The compound 2',3'-dideoxy-2'-beta-fluoroadenosine.
2. The compound 2',3'-dideoxy-2'-beta-fluoroinosine.
3. The compound 2',3'-dideoxy-2'-beta-fluoroguanosine.
4. A composition comprising the compound of claim 1 and an acceptable carrier.

* * * * *